US00PP18712P2

(12) United States Plant Patent
Austin

(10) Patent No.: US PP18,712 P2
(45) Date of Patent: Apr. 8, 2008

(54) SHRUB ROSE PLANT NAMED 'AUSBECKS'

(50) Latin Name: *Rosa hybrida*
Varietal Denomination: AUSbecks

(75) Inventor: David C. H. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 0 days.

(21) Appl. No.: 11/635,254

(22) Filed: Dec. 6, 2006

(51) Int. Cl.
*A01H 5/00* (2006.01)

(52) U.S. Cl. ..... Plt./107
(58) Field of Classification Search ..... Plt./107
See application file for complete search history.

*Primary Examiner*—Kent Bell
*Assistant Examiner*—S. B. McCormick-Ewoldt
(74) *Attorney, Agent, or Firm*—Kauth, Pomeroy, Peck & Bailey LLP

(57) ABSTRACT

Shrub rose plant substantially as herein shown and described, characterized particularly by deep rose-pink, shallow cupped blooms; a strong, spicy, Old Rose fragrance; and vigorous, bushy growth.

1 Drawing Sheet

Genus and species: *Rosa hybrida.*
Variety denomination: 'AUSbecks'.

ORIGIN OF THE INVENTION

The present invention relates to a new and distinct variety of a shrub rose plant named 'AUSbecks' which was originated by me by crossing an unnamed, unpatented seedling with an unnamed, unpatented seedling.

BACKGROUND OF THE INVENTION

The primary objective of this breeding was to produce a very healthy and repeat flowering variety having deep rose-pink blooms and a strong fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Deep rose-pink, shallow cupped blooms.
2. A strong, spicy, Old Rose fragrance.
3. Vigorous, bushy growth.

Asexual reproduction of this new variety by budding, as performed at Albrighton, England, shows that the foregoing and all other characteristics and distinctions come true to form and are established and transmitted through succeeding propagations.

Comparison with Parents

The seed parent has semi-double, lilac blooms whereas 'AUSbecks' has full, double deep rose-pink blooms. The pollen parent has apricot blooms and more upright growth than 'AUSbecks'.

Comparison with Similar Variety

'AUSbite' (U.S. Plant Pat. No. 14,973) has considerably more petals per bloom than 'AUSbecks' and a myrrh fragrance. 'AUSbite' also has taller growth and larger leaves than 'AUSbecks'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling (Unpatented).

FLOWER

Observations made from plants commencing at one year of age grown in a garden environment at Albrighton, England.

Blooming habit: Recurrent. The number of blooms per plant during the growing season is profuse — there are too many to count.

Bud:
*Size.*—About 1.9 cm long and 1.6 cm in diameter when the petals start to unfurl.
*Form.*—The bud form is pointed ovoid.
*Color.*—When sepals first divide, bud color is Red-Purple Group 58A. When half blown, the upper sides of the petals are Red-Purple Group 68B and the lower sides of the petals are Red-Purple Group 62B.
*Sepals.*—Color: Upper surface: Yellow-Green Group 148D. Lower surface: Yellow-Green Group 146B. Length: 1.6 cm. Width: 0.6-0.7 cm. Shape: Subulate.

Surface texture: Upper surface: Pubescent. Lower surface: Smooth. There are three lightly appendaged sepals. There are two unappendaged sepals with canescent edges.

*Receptacle.*—Color: Green Group 143C. Shape: Campanulate. Size: Medium, about 0.9 cm long×0.7 cm wide. Surface: Smooth.

*Peduncle.*—Length: Long, averaging about 8 cm. Surface: Glandular. Color: Yellow-Green Group 146B. Strength: Strong.

Bloom:

*Size.*—Medium. Average open diameter is about 6.3 cm.

*Borne.*—Several together in irregular compound corymb clusters of about five to seven blooms.

*Stems.*—Strength: Normal. Average length is about 50 cm with a diameter of about 0.8 cm.

*Form.*—When first open: Cupped. Permanence: Flattens slightly, outer petal edges curl slightly.

*Petalage.*—Number of petals under normal conditions: 80.

*Color.*—The upper sides of the petals are Red-Purple Group 65A. The reverse sides of the petals are Red-Purple Group N57D. The base of each petal is Yellow Group 4D.

*Variegations.*—None.

*Discoloration.*—The general tonality at the end of the first day is Red-Purple Group 68B. At the end of the third day: Red-Purple Group 73A.

*Fragrance.*—Strong, spicy, Old Rose.

Petals:

*Texture.*—Smooth and slightly leathery at base.

*Size.*—Width: 3.8 cm. Length: 4.4 cm.

*Surface.*—Smooth.

*Shape.*—Broad elliptical. Margin: Some notched, some entire. Apex Shape: Emarginate. Base Shape: Cuneate. Form: Incurved.

*Arrangement.*—Informal.

*Petaloids.*—Number: 12. Color: Anther: Orange Group 26B. Filament: Green-Yellow Group 1D. Petal part: Red-Purple Group N66D. Length: Anther: 3 mm; Filament: 8 mm; Petal part: 8 mm.

*Persistence.*—Petals drop off cleanly before drying.

*Lastingness.*—On the plant: Short (about 2-3 days). As a cut flower: Not tested.

Reproductive parts:

*Stamens.*—Number: 105. Length: 9-10 mm. Anthers: Length: 2 mm. Color: Orange Group 26B. Arrangement: Regular around styles, mixed with petaloids. Filaments: Color: Green-Yellow Group 1D. Length: 7-8 mm. Pollen: Color: Orange Group 26B.

*Pistils.*—Number: 75. Length: 8 mm. Styles: Color: Green-Yellow Group 1D. Length: 7 mm. Stigmas: Color: Yellow Group 12C. Length: 1 mm.

*Hips.*—None observed.

PLANT

*Form.*—Shrub.

*Growth.*—Vigorous, bushy.

*Age at maturity.*—Two years.

*Mature plant.*—Height: 1.25 m. Width: 1.0 m.

*Rootstock.*—'Dr. Huey' in the USA. *Rosa dumetorum* 'Laxa' for the observed plants in the U.K.

Foliage: Number of leaflets on normal mid-stem leaves: 5-7 (including terminal leaflet).

*Size.*—Medium. About 14.4 cm long×10.5 cm wide.

*Quantity.*—Normal. Average number leaves per flowering stem: 8.

*Color.*—New foliage: Upper side: Greyed-Purple Group 187A. Lower side: Greyed-Purple Group 183C. Old foliage: Upper side: Yellow-Green Group 146A. Lower side: Yellow-Green Group 148B.

Leaflets:

*Size.*—About 6 cm long×4.2 cm wide.

*Shape.*—Pointed oval.

*Base shape.*—Rounded.

*Apex shape.*—Acuminate.

*Texture.*—Leathery.

*Edge.*—Serrated.

*Serrations.*—Single, small.

*Petiole.*—Color: Green Group 143C. Length: 4-5 cm. Width: 2 mm. Surface texture: Smooth.

*Petiole rachis.*—Color: Yellow-Green Group 146A upper side, Yellow-Green Group 144A lower side. Underside: Rough with prickles.

*Stipules.*—Length: 1.2 cm, bearded. Color: Yellow-Green Group 144A.

*Auricle shape.*—Subulate. Length: 5 mm. Width: 1 mm at base, tapering to a fine point. Color: Yellow-Green Group 144A.

*Disease resistance.*—Resistant to powdery and downy mildew, blackspot and rust in normal growing conditions.

*Pest resistance.*—Not tested.

*Vein color.*—Yellow-Green Group 144A.

*Venation pattern.*—Reticulate.

Wood:

*New wood.*—Color: Yellow-Green Group 146A. Bark: Rough.

*Old wood.*—Color: Yellow-Green Group 146A. Bark: Rough.

Stems:

*Mature stem.*—Length: 50 cm. Diameter: 8 mm.

*Internode distance.*—6 cm. The above measurements are all variable, depending on growing conditions in a season.

Prickles:

*Quantity.*—On main canes from base: Ordinary, 30 per 30 cm stem length. On laterals from main canes: Ordinary, 15 per 30 cm per stem length.

*Form.*—Hooked downward.

*Length.*—5-7 mm.

*Color when young.*—Greyed-Purple Group 184C.

*Color when mature.*—Greyed-Brown Group 199C.

Small prickles:

*Quantity.*—On main stalks: Many, 10 per 5 cm stem length. (Mainly concentrated at the base and below new shoots.) On laterals: Few, 10 per 30 cm stem length.

*Color when young.*—Greyed-Purple Group 186A.

*Color when mature.*—Greyed-Brown Group 199C.

Winter hardiness: Not tested.

I claim:

1. A new and distinct variety of shrub rose plant substantially as herein shown and described, characterized particularly by deep rose-pink, shallow cupped blooms; a strong, spicy, Old Rose fragrance; and vigorous, bushy growth.

* * * * *

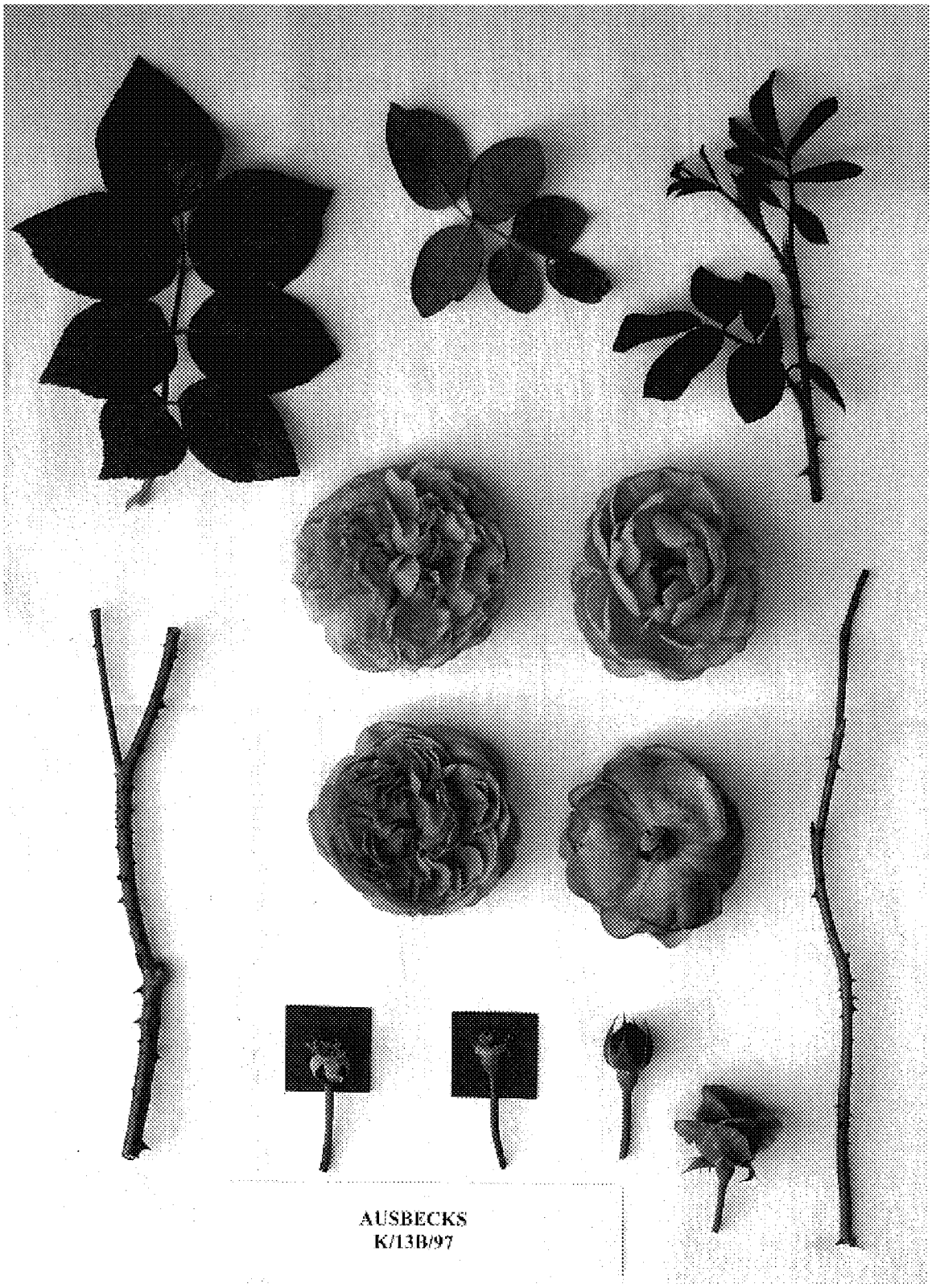
AUSBECKS
K/13B/97